United States Patent [19]

Nagarajan

[11] Patent Number: 4,954,623
[45] Date of Patent: Sep. 4, 1990

[54] RECOVERY OF DIFLUORO SUGAR

[75] Inventor: Ramakrishnan Nagarajan, Indianapolis, Ind.

[73] Assignee: Eli Lilly and Company, Indianapolis, Ind.

[21] Appl. No.: 434,219

[22] Filed: Nov. 13, 1989

Related U.S. Application Data

[63] Continuation-in-part of Ser. No. 325,726, Mar. 20, 1989.

[51] Int. Cl.$^5$ ............................ C07H 1/00; C07H 5/00; C07D 307/00
[52] U.S. Cl. ................................. 536/127; 536/122; 536/18.4; 536/124; 536/23; 536/24; 549/295; 549/324; 549/325
[58] Field of Search ....................... 536/127, 122, 18.4, 536/124, 23, 24; 549/324, 325, 295

[56] References Cited

U.S. PATENT DOCUMENTS

| | | | |
|---|---|---|---|
| 3,227,736 | 1/1966 | Tschesche et al. | 549/324 |
| 3,320,285 | 5/1967 | Martel et al. | 549/324 |
| 4,526,988 | 7/1985 | Hertel | 536/23 |
| 4,692,434 | 9/1987 | Hertel | 536/23 |
| 4,808,614 | 2/1989 | Hertel | 536/24 |

FOREIGN PATENT DOCUMENTS

| | | | |
|---|---|---|---|
| 54-128564 | 10/1979 | Japan | 549/324 |
| 55-122774 | 9/1980 | Japan | 549/324 |

OTHER PUBLICATIONS

Ennifar et al., *J.C.S. Chem. Comm.*, 41–42 (1977).
Codington et al., *Carbohydrate Res. I*, 455–466 (1966).
Yamaguchi et al., *Chem. Pharm. Bull.* 32, 1441–1450 (1984).
Osamu Kitagawa, et al., *Tetrahedron Letters*, 29(15), 1803–1806, (1988).
An and Bobek, *Tetrahedron Letters*, 17(28), 3219–3222, (1986).

Primary Examiner—Ronald W. Griffin
Assistant Examiner—Everett White
Attorney, Agent, or Firm—Joseph A. Jones; Leroy Whitaker

[57] ABSTRACT

A process for recycling the difluoro sugar in the synthesis of 2,2-difluoronucleosides proceeds by removing the base moiety of α-difluoronucleosides by reduction and hydrolysis, followed by oxidation to put the difluro sugar in a form conveniently recycled into the synthesis, and intermediates useful therefor.

30 Claims, No Drawings

RECOVERY OF DIFLUORO SUGAR

CROSS-REFERENCE

This application is a continuation-in-part of copending U.S. application Ser. No. 07/325,726, filed Mar. 20, 1989.

BACKGROUND OF THE INVENTION

The present invention belongs to the fields of pharmaceutical and organic chemistry, and provides an economical process for recovering a valuable by-product in the synthesis of difluoronucleosides.

The difluoronucleosides were first disclosed by Hertel in U.S. Pat. Nos. 4,526,988 and 4,692,434, which are incorporated herein by reference. Hertel taught the synthesis of the difluoronucleosides, and showed that they are active as antivirals. Later, it was learned by Grindey and Hertel that the difluoronucleosides are valuable anticancer drugs, see European Patent Publication 0184365. Research on the difluoronucleosides continues intensively, and it is probable that at least one of them, 2'-deoxy-2',2'-difluorocytidine, will be approved for therapeutic use in cancer patients.

Hertel taught that the β-configuration difluoronucleoside is the more important form, see column 3 of U.S. Pat. No. 4,526,988. Further research has shown that the β-configuration compounds are difficultly obtainable in pure form, and that the available syntheses are likely to produce a mixture of the α- and β-forms.

The difluoronucleosides are made up of a base moiety, which is easily and cheaply prepared, and a difluororibofuranose moiety, which is expensive. The present process provides a convenient route for recovering the difluoro sugar moiety from the α-configuration difluoronucleosides, in the form of an intermediate which is conveniently recycled.

SUMMARY OF THE INVENTION

The present invention provides a process for preparing 2-deoxy-2,2-difluororibopyranose of the formula

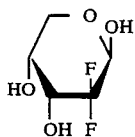
I which comprises reacting an α-difluoronucleoside of the formula

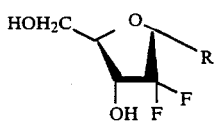
II wherein R is

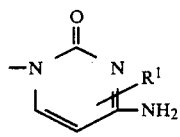
(a)

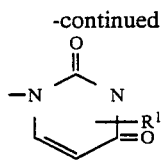
(b)

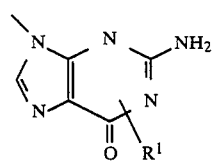
(c)

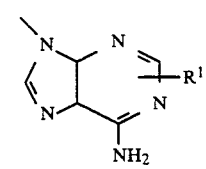
(d)

$R^1$ is hydrogen, $C_1$–$C_3$ alkyl or halo;

with a reducing agent capable of reducing the double bond β to the point of attachment of the R moiety; and hydrolyzing the reduced intermediate in an aqueous acid medium.

The 2-deoxy-2,2-difluororibopyranose so prepared may be isolated by column chromatography or, preferably, by acylating the crude hydrolysate to prepare crystalline triacyl-2-deoxy-2,2-difluororibopyranose;

and treating the triacyl-2-deoxy-2,2-difluororibopyranose with a suitable base to prepare crystalline 2-deoxy-2,2-difluororibopyranose.

The invention also provides a process for preparing a ribofurano-1,4-lactone of the formula

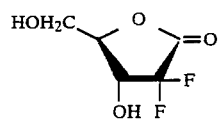
III which comprises the above process, wherein, as an additional step, the 2-deoxy-2,2-difluororibopyranose is oxidized.

Additionally, the invention provides the intermediate 2-deoxy-2,2-difluororibopyranose of formula

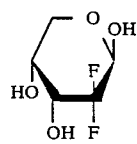
I

DETAILED DESCRIPTION OF THE INVENTION

Throughout this document, all temperatures are described in degrees Celsius. All expressions of proportion, percentage and the like are in weight units, except for mixtures of solvents, which are described in volume units.

In the above formulae, the term $C_1$–$C_3$ alkyl refers to methyl, ethyl, propyl and isopropyl, and the term halo refers to iodo, chloro, bromo and fluoro.

The α-difluoronucleosides which are recycled by the process of the present invention are prepared according to processes taught by U.S. Patent 4,692,434, European Patent Publication 0184365, and European Patent Publication 0211354.

The ribofuranolactone of formula III is shown by Hertel to be a convenient intermediate for the difluoronucleosides, see column 7 of U.S. Pat. No. 4,692,434. Thus, the product of the present process is recycled directly back into the difluoronucleoside synthesis. It is preferred to block the lactone with benzoyl groups on the 3- and 5-hydroxy groups, and the dibenzoylation step is shown below as Preparation 1.

While all aspects of the process as stated above are valuable, there are certain aspects which are particularly useful and therefore are preferred. Those aspects are set out briefly below. It will be understood that different preferred aspects of the invention may be combined to create further, limited, more highly preferred statements of the process.

(A) Use of difluoronucleosides wherein $R^1$ is hydrogen;
(B) Use of difluoronucleosides wherein R is of formula a;
(C) Use of difluoronucleosides wherein $R^1$ is methyl;
(D) Reduction by catalytic hydrogenation;
(E) Hydrolyzing in the presence of a mineral acid;
(F) Hydrolyzing in the presence of hydrochloric acid;
(G) Acylating the hydrolysate with an acid anhydride;
(H) Acylating the hydrolysate in the presence of an acylation catalyst;
(I) Acylating the hydrolysate with acetic anhydride in pyridine;
(J) Crystallization of the triacyl-2-deoxy-2,2-difluororibopyranose from an inert solvent;
(K) Deacylation of the triacyl-2-deoxy-2,2-difluororibopyranose with a base;
(L) Deacylation of the triacyl-2-deoxy-2,2difluororibopyranose with triethylamine;
(M) Oxidizing in the presence of an elemental halogen;
(N) Oxidizing in the presence of elemental bromine.

It is believed that the nature of the starting compounds of the process is entirely clear to any chemist, but some further information will be given to assure that the reader is perfectly clear. The following table fully describes a group of starting compounds, by the identity of the R and $R^1$ groups and the location of $R^1$.

| R | $R^1$ |
|---|---|
| a | hydrogen |
| a | 3-methyl |
| a | 2-ethyl |
| a | 3-isopropyl |
| a | 2-fluoro |
| a | 2-chloro |
| a | 3-iodo |
| b | 3-propyl |
| b | 3-bromo |
| b | 2-methyl |
| b | 2-chloro |
| c | 3-methyl |
| c | 3-fluoro |
| c | 8-propyl |
| c | 8-iodo |
| b | hydrogen |
| c | hydrogen |
| d | hydrogen |
| d | 2-ethyl |
| d | 2-bromo |
| d | 8-methyl |
| d | 8-chloro |

In the first step of the present process, the α-difluoronucleoside is reduced with a reducing agent capable of reducing the double bond, in the base moiety of the nucleoside, which is β to the point of attachment of that base moiety to the sugar. Thus, if the base moiety were numbered with point of attachment as "1", the double bond referred to would be the 2,3-bond. It is preferred to carry out the reduction by means of catalytic hydrogenation, using a noble metal catalyst such as platinum oxide, platinum-on-carbon and the like. Such hydrogenations are usually carried out near ambient temperature, such as from 0° to 50° and at moderate hydrogen pressures in the range of about 1–5 atmospheres. Catalytic hydrogenations are usually carried out in alkanol solvents, especially in ethanol, and under acid conditions. It is preferable to use comparatively weakly ionized acids such as acetic acid and the like in the hydrogenation medium.

The reduced α-difluoronucleoside is then hydrolyzed under acid conditions, which step leaves the reduced base from the sugar moiety and affords the crystalline difluororibopyranose of formula 1. The hydrolysis is most preferably carried out in the presence of an aqueous mineral acid, at a moderately elevated temperature such as the reflux temperature of the reaction mixture. Dilute hydrochloric acid is believed to be the most preferable hydrolyzing agent. However, the other strong mineral acids such as nitric acid, sulfuric acid and the like may equally be used, as can such strong organic acids as sulfonic acid, methanesulfonic acid, toluenesulfonic acid, formic acid and the like. The general temperature range for hydrolyses is from about the ambient temperature to about 150°; operation under pressure is obviously required if temperatures above the ambient pressure boiling point are to be used.

The reduction and hydrolysis steps may be carried out without intermediate isolation of the reduced α-difluoronucleoside, and such operation is preferred. After the hydrolysis step, however, it is advisable to isolate the 2-deoxy-2,2-difluororibopyranose. Example 1 below illustrates a liquid chromatography process which conveniently isolates the pyranose.

As an alternative to liquid chromatograpy, the crude hydrolysate may be treated with an acylating agent, such as an appropriate acid halide or acid anhydride. The reaction may be performed in the presence of an acylation catalyst such as pyridine, dimethylaminopyridine and the like. Acetic anhydride in the presence of pyridine are an example of preferred acylating conditions. The acylation is conveniently performed at or near ambient temperature. After extraction and aqueous work-up, the triacyl-2-deoxy-2,2-difluororibopyranose is crystallized from an inert solvent, preferably anhydrous ethanol.

The triacyl-2-deoxy-2,2-difluororibopyranose may now be deacylated. Acyl groups are removed by simple hydrolysis with strong or moderately strong bases such as alkali metal hydroxides, hydrazine, hydroxylamine, ammonia, alkali metal amides, basic exchange resins, secondary amines and tertiary amines, such as triethylamine. At least one equivalent of base is required for each protecting group. Such hydrolyses are conveniently carried out in hydroxylic solvents, especially aqueous alkanols. The reactions may also be carried out, however, in any convenient solvent, such as polyols including ethylene glycol, ethers such as tetrahydrofuran and the like, ketones such as acetone and methyl ethyl ketone and other polar solvents such as dimethylsulfoxide. The deacylation is conveniently performed at ambient temperature. The reaction mixture is then concentrated under reduced pressure and 2-deoxy-2,2-difluororibopyranose recovered by crystallization from an inert solvent, preferably methanol.

In the final step of the process of this invention, the pyranose is oxidized to prepare 2-deoxy-2,2-difluororibofurano-1,4-lactone of formula III above. Severe oxidizing conditions are not required in this step. The oxidation is conveniently carried out with elemental bromine in aqueous medium. The oxidation may also be carried out, for example, with hypochlorite, or with elemental chlorine, which is equivalent to hypochlorite, of course. The oxidation may also be done by electrolysis in the presence of alkaline metal bromides as illustrated in the example below, and those are the preferred conditions. The oxidized product, the lactone, is then purified and isolated to remove inorganic ions and salts, and is then recycled into the synthesis of difluoronucleosides as described in the Hertel patent. The hydroxy groups of the lactone must be blocked, and, as mentioned above, it is preferred to use benzoyl blocking groups and to carry out the dibenzoylation as shown below in Preparation 1.

EXAMPLE 1

Reduction

A 122.8 g portion of α-1-(2-oxo-4-amino-1H-pyrimidin-1-yl)-2-deoxy-2,2-difluororibofuranose, hydrochloride salt, was dissolved in 1539 ml of acetic acid and 1539 ml of ethanol, and 73.7 g of platinum dioxide was added to the mixture in a hydrogenation bomb. The bomb was shaken for 16 hours under 4 atmospheres of hydrogen pressure, and the reaction mixture was then evaporated under vacuum to an oily residue. The residue was taken up in 150 ml of water, was frozen, and was lyophilized under vacuum. The lyophilization was repeated a second time, to obtain a residue of thin, oily material containing some white solids, amounting to 195 g.

Hydrolysis

The residue from Example 1 was dissolved in 500 ml of 1N hydrochloric acid, and was stirred on a steam bath for 7.5 hours. The hydrolysate was then cooled to room temperature and lyophilized to obtain about 250 g of syrupy product.

This product was purified by high performance liquid chromatography, using a Waters instrument and silica gel columns. The chromatography was carried out on 50 g portions of the residue, each of which was eluted with 8 liters of a gradient solvent, beginning with ethyl acetate and proceeding to 15% methanol in ethyl acetate. The elution rate was 250 ml/minute, and 250 ml fractions were collected. The effluent was monitored by ultraviolet at 280 nm, with the addition of elemental iodine. The eluates were also observed by thin layer chromatography on silica gel, using 3:1 ethyl acetate:methanol as the solvent. The product-containing fractions were combined, and the product was crystallized from 150 ml of hot methanol to obtain 55.6 g of 2-deoxy-2,2-difluororibopyranose, yield 80%, m.p. 146°–148° C. Field desorption mass spectrum $MH^+ = 171$. $^1H$ NMR (300 MHz, DMSO-$d_6$): δ7.15 (1-OH, d, J=6.7 Hz), 5.61 (3-OH, d, J=6.0), 4.87 (4-OH, d, J=6.7), 4.84 (1-H, m, $J_{1,F}=10.4$, 2.0), 3.85 (3-H, m, $J_{3,F}=15.1$, 5.7; $J_{3,4}=3.7$), 3.71 (4-H, m, $J_{4,5}=7.4$), 3.71 (H-5′, m, $J_{5,5'}=12.1$), 3.49 (H-5, m, $J_{5,5'}=12.1$).

The structure of 2-deoxy-2,2-difluororibopyranose was determined by x-ray crystallography.

Acetylation

A 69.7 g portion of the crude hydrolysis product (52% 2-deoxy-2,2-difluororibopyranose) was dissolved in 200 ml pyridine with warming on a steam bath. To this was then added 200 ml acetic anhydride and the reaction mixture was allowed to stir at room temperature for 18 hours. The reaction mixture was then concentrated under reduced pressure and the brown, oily residue redissolved in 500 ml of dichloromethane. This solution was poured into 500 ml of ice water and stirred vigorously for one hour. The organic layer was separated and washed successively with 300 ml each of 1N hydrochloric acid, saturated aqueous sodium bicarbonate and saturated aqueous sodium chloride. The remaining organic solution was dried over sodium sulfate and concentrated under reduced pressure to give a light yellow oil which crystallized on standing. This residue was crystallized from anhydrous ethanol to give 28.19 g (44.6%) 1,3,4-triacetoxy-2-deoxy-2,2-difluororibopyranose as a crystalline solid.

m.p. = 148°–149° C.

MS(FD): $M^+ + Na^+ = 319$.

$^1H$-NMR(270 MHz, CDCl$_3$): δ6.19 (1-H, m, $J_{1,F}=3.05$, 5.49 Hz), 5.46 (3-H, m, $J_{3,4}=3.97$, $J_{3,F}=7.93$, 18.62), 5.38 (4-H, m, $J_{4,5}=2.14$, $J_{4,5'}=2.44$), 4.12 (5-H, d, $J_{5,5'}=13.43$), 3.90 (5′-H, d, $J_{5',5}=13.43$), 2.20, 2.15 & 2.14 (CH$_3$(acetyl), s).

$^{13}C$-NMR(270 MHz, CDCl$_3$): δ170.14, 169.37 and 167.91 Hz,(O=C(acetyl), s), 113.30 (2-C, d, $J_{2,F}=254.31$), 89.86 (1-C, m, $J_{1,F}=29.59$, 37.92), 65.96 (3-C, m, $J_{3,F}=18.50$, 22.19), 67.30 (4-C, d, $J_{4,F}=4.62$), 62.65 (5-C, s), 20.28, 20.54 and 20.28 (CH$_3$(acetyl), s).

Deacetylation

To a solution of 10.53 g (33.7 mmol) 1,3,4-triacetoxy-2-deoxy-2,2-difluororibopyranose in methanol (35 ml) and water (10 ml) was added triethylamine (16 ml, 114.8 mmol) and the solution was stirred at room temperature for 3 days. The reaction mixture was then concentrated under reduced pressure and the resulting residue stirred with dichloromethane (50 ml) for 18 hours. The dichloromethane phase was decanted off and the remaining residue was again treated with dichloromethane (50 ml) for 18 hours. The dichloromethane phase was decanted off and the residue was concentrated under reduced pressure to remove any residual dichloromethane and was then dissolved in methanol (20 ml). The solution was then filtered to remove any insoluble material and the volume reduced by 50% on the steambath. After cooling to room temperature the solution was cooled to 0° C. for 18 hours. Crystalline 2-deoxy-2,2-difluororibopyranose (3.83 gm, 63.3%) was recovered by filtration. m.p. = 140°–142° C. MS(FD): $M^+ + 1 = 171$ TLC(silica gel plate, EtOAc): Same $R_f$ as material recovered by chromatography as described under Hydrolysis above.

Oxidation

A 100 ml beaker was charged with a 2.125 gm portion of 2-deoxy-2,2-difluororibopyranose, 0.40 gm calcium bromide and 0.675 gm calcium carbonate in 50 ml of water. Into this suspension were placed 4 1"×4" graphite electrodes which had been precleaned by washing with 1N hydrochloric acid followed by deionized water. Constant current was applied at 25 mA for 26 hours at which time 2,386 coulombs (99% theoretical) had passed as counted on an ESC coulometer. The reaction mixture was then filtered and concentrated under vacuum. The residue was redissolved in deionized water (50 ml) and then 0.875 gm oxalic acid were added. The suspension was filtered and the filtrate then treated with a slurry of silver carbonate (freshly prepared from 2.9 gm silver nitrate and 1.45 gm sodium bicarbonate). The insoluble salts were filtered and the filtrate was passed through a column containing 50 ml of Dowex 50W-8x cation exchange resin (H+). The clear eluate was then lyophilized several times in the presence of dioxane to yield 2.08 gm 2-deoxy-2,2-difluoro- ribofurano-1,4-lactone as a light yellow syrup.

Alternatively, the oxidation was performed by dissolving a 10.1 g portion of 2-deoxy-2,2-difluororibopyranose with 29 g of barium benzoate in 750 ml of water. The solution was cooled to 0° before adding 3.6 ml of bromine and the mixture was stirred in the dark for 40 hours. The precipitates that had formed during the reaction were filtered off and excess bromine was removed from the filtrate by placing it under vacuum until the orange color disappeared. The colorless solution was then treated with 140 ml of 1N sulfuric acid and filtered, and the resulting filtrate extracted with 500 ml of methylene chloride. The organic layer was discarded, and the aqueous layer was mixed with a slurry of silver carbonate (freshly prepared from 24 g of silver nitrate and 12 g of sodium bicarbonate). The insoluble salts were filtered away, and the filtrate was passed through a 1.75 cm×25 cm column of Dowex-X8 cation exchange resin to remove silver and barium salts. The recovered eluates were then lyophilized several times in the presence of dioxane to yield 8.5 g of 2-deoxy-2,2-difluororibofurano-1,4-lactone. FDMS MH+=169. IR (KBr disc): $\nu$C=0 at 1771 and 1871 cm$^{-1}$ ($\gamma$-lactone).

PREPARATION 1

Dibenzoylation

To a solution of 885 mg of 2-deoxy-2,2-difluororibofurano-1,4-lactone in 25 ml of pyridine was added 2 ml of lutidine and 366 mg of 4-dimethylaminopyridine. The mixture was cooled to 0° and then a solution of 1.2 ml of benzoyl chloride in 20 ml of methylene chloride was added dropwise. The ice bath was removed and the reaction mixture was refluxed for 1 hour and evaporated to dryness. The recovered material was then taken up in 50 ml of methylene chloride and washed sequentially with 75 ml of 1N hydrochloric acid, 25 ml of saturated sodium bicarbonate solution and 50 ml of saturated sodium chloride solution. The organic layer was dried over sodium sulfate and concentrated to dryness. The residue was 1.48 g of pale yellow oily material. Crystallization from methylene chloride-ether yielded 335 mg (17% yield) of 3,5-dibenzoyl-2-deoxy-2,2-difluororibofurano-1,4-lactone, m.p. 116°–117°. FDMS MH+=377. $^1$H NMR (300 MHz, CDCl$_3$) $\delta$ 8.07–7.45 (2 OCOC$_6$H$_5$); 5.75 (H-3, J$_{3,F}$=6.10, 12.21 Hz, J$_{3,4}$=4.58); 4.99 (H-4, J$_{4,5}$=3.66, J$_{4,5'}$=4.58); 4.77 (H-5, J$_{5,5'}$=12.51); 4.68 (H-5').

I claim:

1. A process for preparing 2-deoxy-2,2-difluororibopyranose of the formula

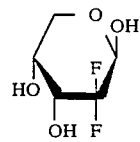

which comprises reacting an $\alpha$-difluoronucleoside of the formula

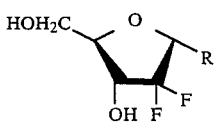

wherein R is

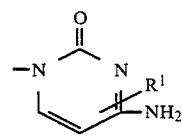

(a)

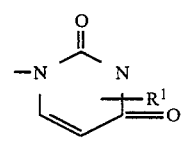

(b)

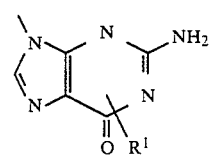

(c)

or

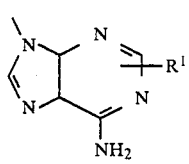

(d)

R$^1$ is hydrogen, C$_1$–C$_3$ alkyl or halo;
  with a reducing agent capable of reducing the double bond $\beta$ to the point of attachment of the R moiety; and hydrolyzing the reduced intermediate in an aqueous acid medium.

2. A process of claim 1 wherein the reduction is carried out by catalytic hydrogenation.

3. A process of claim 2 wherein the hydrolysis is carried out in the presence of a mineral acid.

4. A process of claim 3 wherein the $\alpha$-di-fluoronucleoside is a compound wherein R is of formula a.

5. A process of claim 4 wherein the $\alpha$-di-fluoronucleoside is a compound wherein R$^1$ is hydrogen.

6. A process of claim 1 wherein the hydrolysate is purified by chromatography.

7. A process of claim 1 wherein the hydrolysate is purified by acylating the hydrolysate with an acid halide or acid anhydride to prepare a crystalline triacyl-2-deoxy-2,2-difluororibopyranose;

and treating the triacyl-2,2-difluororibopyranose with a suitable base to prepare crystalline 2-deoxy-2,2-difluororibopyranose.

8. A process of claim 7 wherein the acylating agent is acetic anhydride.

9. A process of claim 7 wherein the acylation is performed in the presence of an acylation catalyst.

10. A process of claim 9 wherein the acylation catalyst is pyridine.

11. A process of claim 10 wherein the base is triethylamine.

12. A process of claim 1 wherein the α-di-fluoronucleoside is a compound wherein R is of formula a.

13. A process of claim 12 wherein the α-di-fluoronucleoside is a compound wherein R¹ is hydrogen.

14. A process of claim 1 wherein the α-di-fluoronucleoside is a compound wherein R¹ is hydrogen.

15. A process for preparing 2-deoxy-2,2-difluororibofurano-1,4-lactone of the formula

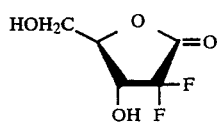   III comprising reacting an α-difluoronucleoside of the formula

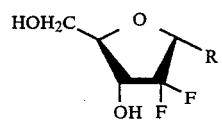   II wherein R is

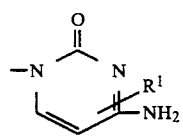   (a)

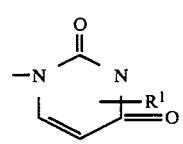   (b)

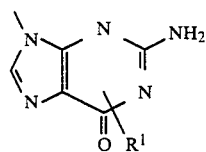   (c)

or

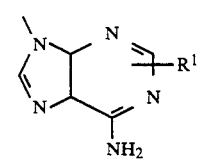   (d)

R¹ is hydrogen, $C_1$-$C_3$ alkyl or halo;
with a reducing agent capable of reducing the double bond β to the point of attachment of the R moiety;
hydrolyzing the reduced intermediate in an aqueous acid medium;
and oxidizing the pyranose.

16. A process of claim 15 wherein the reduction step is carried out by catalytic hydrogenation.

17. A process of claim 16 wherein the hydrolysis step is carried out in the presence of a mineral acid.

18. A process of claim 17 wherein the oxidation step is carried out in the presence of an elemental halogen.

19. A process of claim 17 wherein the α-difluoronucleoside is a compound wherein R is of formula a.

20. A process of claim 19 wherein the α-di-fluoronucleoside is a compound wherein R¹ is hydrogen.

21. A process of claim 15 wherein the hydrolysate is purified by chromatography.

22. A process of claim 15 wherein the hydrolysate is purified by acylating the hydrolysate with an acid halide or acid anhydride to prepare a crystalline triacyl-2-deoxy-2,2-difluororibopyranose;

and treating the triacyl-2,2-difluororibopyranose with a suitable base to prepare crystalline 2-deoxy-2,2-difluororibopyranose.

23. A process of claim 22 wherein the acylating agent is acetic anhydride.

24. A process of claim 22 wherein the acylation is performed in the presence of an acylation catalyst.

25. A process of claim 24 wherein the acylation catalyst is pyridine.

26. A process of claim 25 wherein the base is triethylamine.

27. A process of claim 15 wherein the α-di-fluoronucleoside is a compound wherein R is of formula a.

28. A process of claim 27 wherein the α-di-fluoronucleoside is a compound wherein R¹ is hydrogen 29. A process of claim 15 wherein the α-di-fluoronucleoside is a compound wherein R¹ is hydrogen.

30. An intermediate of formula

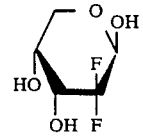   I

* * * * *